US010091256B2

(12) United States Patent
Mayer et al.

(10) Patent No.: US 10,091,256 B2
(45) Date of Patent: *Oct. 2, 2018

(54) ACCESS CHANGE FOR RE-ROUTING A CONNECTION

(71) Applicant: Nokia Technologies Oy, Espoo (FI)

(72) Inventors: Georg Mayer, Vienna (AT); Jari Mutikainen, Lepsama (FI); Peter Leis, Penzberg (DE)

(73) Assignee: Nokia Technologies Oy, Espoo (FI)

( * ) Notice: Subject to any disclaimer, the term of this patent is extended or adjusted under 35 U.S.C. 154(b) by 0 days.

This patent is subject to a terminal disclaimer.

(21) Appl. No.: 15/642,193

(22) Filed: Jul. 5, 2017

(65) Prior Publication Data

US 2017/0302706 A1 Oct. 19, 2017

Related U.S. Application Data

(63) Continuation of application No. 13/148,018, filed as application No. PCT/FI2009/050999 on Dec. 14, 2009, now Pat. No. 9,729,587.

(51) Int. Cl.
*G06F 15/16* (2006.01)
*H04L 29/06* (2006.01)
(Continued)

(52) U.S. Cl.
CPC ...... *H04L 65/1083* (2013.01); *H04L 65/1006* (2013.01); *H04M 7/128* (2013.01); *H04W 76/18* (2018.02); *H04W 36/0022* (2013.01)

(58) Field of Classification Search
CPC .......... H04L 65/1083; H04L 65/1006; H04W 76/18; H04W 36/0022; H04M 7/128
(Continued)

(56) References Cited

U.S. PATENT DOCUMENTS

| 6,778,492 B2 | 8/2004 | Charny et al. |
| 7,366,182 B2 | 4/2008 | O'Neill |

(Continued)

FOREIGN PATENT DOCUMENTS

| CN | 101296177 A | 10/2008 |
| EP | 1931094 A1 | 6/2008 |

(Continued)

*Primary Examiner* — Sm Rahman
(74) *Attorney, Agent, or Firm* — Mintz Levin Cohn Ferris Glovsky and Popeo, P.C.

(57) ABSTRACT

There is proposed a method and corresponding apparatuses allowing a change from a packet switched communication domain to a circuit switched communication domain. When a user equipment as a connection terminating point receives a connection initialization message with a media flow, such as audio, which cannot be delivered by the packet switched access, it sends a specific response rejecting the connection via the packet switched access to an application server for service centralization and continuity. In the application server, it is checked whether several conditions are met in order to determine whether the communication connection comprising the media flow is allowed to be changed to the circuit switched domain. If yes, the communication connection is changed from the packet switched communication domain to the circuit switched communication domain.

20 Claims, 6 Drawing Sheets

(51) Int. Cl.
*H04M 7/12* (2006.01)
*H04W 76/18* (2018.01)
*H04W 36/00* (2009.01)

(58) Field of Classification Search
USPC .......................................................... 709/227
See application file for complete search history.

(56) References Cited

U.S. PATENT DOCUMENTS

| | | |
|---|---|---|
| 7,953,416 B2 | 5/2011 | Gonen et al. |
| 2002/0110104 A1 | 8/2002 | Surdila et al. |
| 2003/0223426 A1 | 12/2003 | Requena et al. |
| 2004/0184419 A1 | 9/2004 | Park |
| 2005/0077546 A1 | 4/2005 | Neaves |
| 2007/0053343 A1 | 3/2007 | Suotula et al. |
| 2007/0218932 A1* | 9/2007 | Sung .................. H04W 72/005 455/518 |
| 2008/0037494 A1 | 2/2008 | Hietalahti et al. |
| 2008/0080428 A1 | 4/2008 | Jappila et al. |
| 2008/0114881 A1* | 5/2008 | Lee .......................... H04L 51/36 709/227 |
| 2008/0165764 A1 | 7/2008 | Mutikainen et al. |
| 2008/0267171 A1 | 10/2008 | Buckley et al. |
| 2009/0093237 A1 | 4/2009 | Levenshteyn et al. |
| 2009/0182819 A1 | 7/2009 | Krantz et al. |
| 2010/0153726 A1 | 6/2010 | Liu et al. |

FOREIGN PATENT DOCUMENTS

| | | |
|---|---|---|
| GB | 2398458 A | 8/2004 |
| WO | WO-2004112415 A2 | 12/2004 |
| WO | WO-2005025196 A1 | 3/2005 |
| WO | WO-2005109796 A1 | 11/2005 |
| WO | WO-2009002114 A2 | 12/2008 |
| WO | WO-2010089445 A1 | 8/2010 |

* cited by examiner

ACCESS CHANGE FOR RE-ROUTING A CONNECTION

This Application is a Continuation of application Ser. No. 13/148,018 filed on Aug. 4, 2011, which claims priority benefit to PCT Application No. PCT/FI2009/050999, filed Dec. 14, 2009, which claims priority benefit from PCT Application No. PCT/EP2009/051263, filed Feb. 4, 2009. The entire contents of these applications are incorporated herein by reference in their entirety.

BACKGROUND OF THE INVENTION

Field of the Invention

The present invention relates to a mechanism for changing an access or communication connection domain for re-routing a connection. In particular, the present invention relates to a mechanism for changing from a specific first communication domain, such as a Packet Switched (PS) domain, to a second communication domain, such as a Circuit Switched (CS) domain, in a terminating session setup procedure.

Related Prior Art

In the last years, an increasing extension of communication networks, e.g. of wire based communication networks, such as the Integrated Services Digital Network (ISDN), or wireless communication networks, such as the cdma2000 (code division multiple access) system, cellular 3rd generation (3G) communication networks like the Universal Mobile Telecommunications System (UMTS), cellular 2nd generation (2G) communication networks like the Global System for Mobile communications (GSM), the General Packet Radio System (GPRS), the Enhanced Data Rates for Global Evolutions (EDGE), or other wireless communication system, such as the Wireless Local Area Network (WLAN) or Worldwide Interoperability for Microwave Access (WiMax), took place all over the world. Various organizations, such as the 3rd Generation Partnership Project (3GPP), Telecoms & Internet converged Services & Protocols for Advanced Networks (TISPAN), the International Telecommunication Union (ITU), $3^{rd}$ Generation Partnership Project 2 (3GPP2), Internet Engineering Task Force (IETF), the IEEE (Institute of Electrical and Electronics Engineers), the WiMax Forum and the like are working on standards for telecommunication network and access environments.

Generally, for properly establishing and handling a communication connection between network elements such as a user equipment (UE) and another communication equipment or user equipment, a database, a server, etc., one or more intermediate network elements such as control network elements, support nodes or service nodes are involved.

One important application is multimedia communication services. A multimedia call is a communication where, for example, audio (voice), text, video and picture are used simultaneously. Multimedia calls generally require the transmission of several different types of data (video, audio, and the like) in parallel, and these data are to be transmitted and received by various different types of communication equipments or network elements, so that it is required that plural communication protocols are negotiated and appropriate parameters for the communication are adjusted.

A current technology to merge the Internet with the cellular telecommunication world is the Internet Protocol (IP) Multimedia Subsystem IMS. IMS is a standardized architecture for operators intending to provide mobile and fixed multimedia services. IMS uses a Voice over IP (VoIP) implementation based on a 3GPP standardized implementation of Session Initiation Protocol (SIP) and runs over the standard Internet Protocol (IP). Both PS and CS communication systems are supported.

As a part of the signaling mechanisms used between the IMS and an user equipment the Session Initiation Protocol (SIP) is used. Details of the structure and procedures executed in IMS are described in the related standards and are commonly known to a person skilled in the art so that a description thereof is omitted herein for the sake of simplicity.

However, it is necessary to ensure interworking between the both CS and PS systems so that an end user experience is not jeopardized.

The IMS provides several services, such as IMS Centralized Services (ICS). ICS provides communication services such that all services, and service control, are based on IMS mechanisms and enablers. It enables IMS services when using CS access for the media bearer.

With ICS, the user services are provided by IMS. User sessions are controlled in IMS via PS or CS access. When using a CS access network, or when using a PS access network that does not support the full duplex speech component of an INS service, the CS core network is utilized to establish a circuit bearer for use as media for IMS sessions. On the other hand, if the PS access network does support, for example, the full duplex speech component of an IMS service then standard IMS session procedures may be used.

As mentioned above, the ICS provides mechanisms to support the use of CS media bearer for IMS sessions. With ICS, IMS sessions using CS media are treated as standard IMS sessions for the purpose of service control and service continuity. The ICS further defines signaling mechanisms between the UE and IMS for transport of information required for service continuity when using CS access for media transport.

IMS as defined by 3GPP supports, in connection with ICS, so-called Single Radio Voice Call Continuity (SR-VCC) where a handover to a CS access is initiated and controlled by ICS. For a proper change of the communication access or domain, such as from a PS domain to a CS domain, several requirements are to be considered. One of the required features is an UE-assisted domain selection for terminating requests. For these cases, in ICS standards, a terminating session setup procedure is defined. In this procedure, it is assumed that the incoming session is delivered over, for example, Gm reference point (signaling interface between the UE and the IMS, which is based on the protocols SIP and SDP) using only PS and the UE decides to use the CS domain. Hence, the session should be set-up by using the CS domain. This may occur, for example, when the UE detects that the PS domain is not capable for audio (speech), i.e. that a corresponding (audio) media flow can not be delivered, so that the UE decides to use the CS domain.

According to the ICS standard, the terminating session setup procedure comprises the following steps. A terminating side Service Centralization and Continuity Application Server (SCC AS) receives a connection initialization message (SIP INVITE message) from a calling UE via a Serving Call Session Control Function (S-CSCF). The SCC AS decides to deliver the call via PS access (PS domain). When the terminating node, i.e. the called UE, receives the INVITE message and detects that the PS domain is not voice capable (e.g. when it is located in a GSM EDGE Radio Access Network (GERAN)), the UE rejects the INVITE. It is further defined in the ICS standard that then the SCC AS sets-up an INVITE towards CSRN (CS routing number, based on which the new call will be routed the CS domain access of the UE), which then gets interworked at an involved Media Gateway Control Function of the called UE (B-MGCF) into a CS SETUP towards the UE.

However, in the present standard, the terminating session setup procedure is not optimized. For example, it is not solved in which way the UE can indicate towards the SCC-AS that the call should be routed to the CS-side of the same UE.

One possible way to solve this is, for example, to let the UE respond with a message indicating that another service is required, such as a SIP 380 response, including an indication in form of an XML indication (extended mark-up language). However, for such an approach, additional standardization work is necessary.

SUMMARY OF THE INVENTION

Thus, it is an object of the invention to provide an improved mechanism for changing an access or communication connection domain for re-routing a connection.

This object is achieved by the measures defined in the attached claims.

In particular, according to one example of an aspect of the proposed solution, there is provided, for example, an apparatus comprising a transmitter configured to transmit a connection initialization request message to a communication connection terminating node for initializing a communication connection in a first communication domain, a receiver configured to receive a response to the connection initialization request message, the response indicating a rejection of a media flow type of the communication connection in the first communication domain and comprising a predetermined indication portion, a processor configured to process the received response, wherein said processor is further configured to check whether a predetermined condition set is met, and, if the predetermined condition set is met, to cause a transmission of another connection initialization request message to the communication connection terminating node for initializing a communication connection in a second communication domain with the rejected media flow type of the communication connection.

Furthermore, according to another example of an aspect of the proposed solution, there is provided, for example, a method comprising transmitting a connection initialization request message to a communication connection terminating node for initializing a communication connection in a first communication domain, receiving a response to the connection initialization request message, the response indicating a rejection of a media flow type of the communication connection in the first communication domain and comprising a predetermined indication portion, processing the received response, checking whether a predetermined condition set is met, and, if the predetermined condition set is met, transmitting another connection initialization request message to the communication connection terminating node for initializing a communication connection in a second communication domain with the rejected media flow type of the communication connection.

According to further refinements, these examples may comprise one or more of the following features:

the processor or processing may be further configured, if the predetermined condition set is not met, to cause a transmission of a message indicating the rejection of the communication connection to a communication connection originating node;

the predetermined indication portion may comprise an information that a contact address of the communication connection terminating node is temporarily changed; then the predetermined indication portion may further comprise address information included in the connection initialization request message, wherein then the processor or processing may be further configured to determine on the basis of the address information that the communication connection is to be re-routed to the same communication connection terminating node in the second communication domain;

alternatively, the predetermined indication portion may comprise an information that a communication connection attempt is not acceptable here;

the predetermined condition set may comprise at least one of a condition that the connection initialization request message includes a parameter indicating the later rejected media flow type of the communication connection, a condition that the response message indicates a failure to deliver to the communication connection terminating node, a condition that the response message does not indicate that a user of the communication connection terminating node performed an operation to not accept the communication connection or that the communication connection terminating node is busy, a condition that the response message does not indicate another service specific action, a condition that a local configuration for the called communication connection terminating node is present in the apparatus, which allows a re-routing to the second communication domain, and a condition that an ability of a communication network portion leading to the communication connection terminating node to deliver the media flow type to the communication connection terminating node in the second communication domain is assumed;

the first communication domain may be based on a packet switched transmission and the second communication domain may be based on a circuit switched transmission;

the specific media flow type may be an audio media flow type;

the apparatus or method may be part of an application server for service centralization and continuity.

Moreover, according to another example of an aspect of the proposed solution, there is provided, for example, an apparatus comprising a receiver configured to receive a connection initialization request message sent to a communication connection terminating node for initializing a communication connection in a first communication domain, a processor configured to process the connection initialization request message, wherein the processor is further configured to determine whether a media flow type of the communication connection in the first communication domain to the communication connection terminating node is not possible, and if this is not possible, the processor is configured to cause a transmitter to transmit a response to the connection initialization request message, the response indicating a rejection of a media flow type of the communication connection in the first communication domain and comprising a predetermined indication portion indicating a re-routing request of the communication connection to a second communication domain.

Moreover, according to another example of an aspect of the proposed solution, there is provided, for example, a method comprising receiving a connection initialization request message sent to a communication connection terminating node for initializing a communication connection in a first communication domain, processing the connection initialization request message, determining whether a media flow type of the communication connection in the first communication domain to the communication connection terminating node is possible, and if this is not possible transmitting a response to the connection initialization request message, the response indicating a rejection of a media flow type of the communication connection in the first communication domain and comprising a predetermined indication portion indicating a re-routing request of the communication connection to a second communication domain.

According to further refinements, these examples may comprise one or more of the following features:

the predetermined indication portion may comprise an information that a contact address of the communication connection terminating node is temporarily changed; then, the predetermined indication portion may further comprise address information included in the connection initialization request message;

alternatively, the predetermined indication portion may comprise an information that a communication connection attempt is not acceptable here;

the first communication domain may be based on a packet switched transmission and the second communication domain may be based on a circuit switched transmission;

the specific media flow type may be an audio media flow type;

the apparatus or method may be part of the communication connection terminating node including a user equipment; alternatively, the apparatus or method may be part of a proxy node connected with the communication connection terminating node.

By virtue of the proposed solutions, it is possible to provide a method and a corresponding apparatus which provide a mechanism for changing an access or communication connection domain for re-routing a connection which can be based on existing signaling protocols, such as on existing SIP protocol elements like SIP 302 or SIP 488. This facilitates the implementation of the proposed mechanism in existing network elements, such as the UE or the SCC AS, and does not require complex standard changes or new protocol extensions. For example, in case of the SCC AS, only the related trigger points need to be set to route to the CS domain (CSRN). Other network elements are not affected by the proposed mechanism.

The above and still further objects, features and advantages of the invention will become more apparent upon referring to the description and the accompanying drawings.

DESCRIPTION OF PREFERRED EMBODIMENTS

Figure 1:
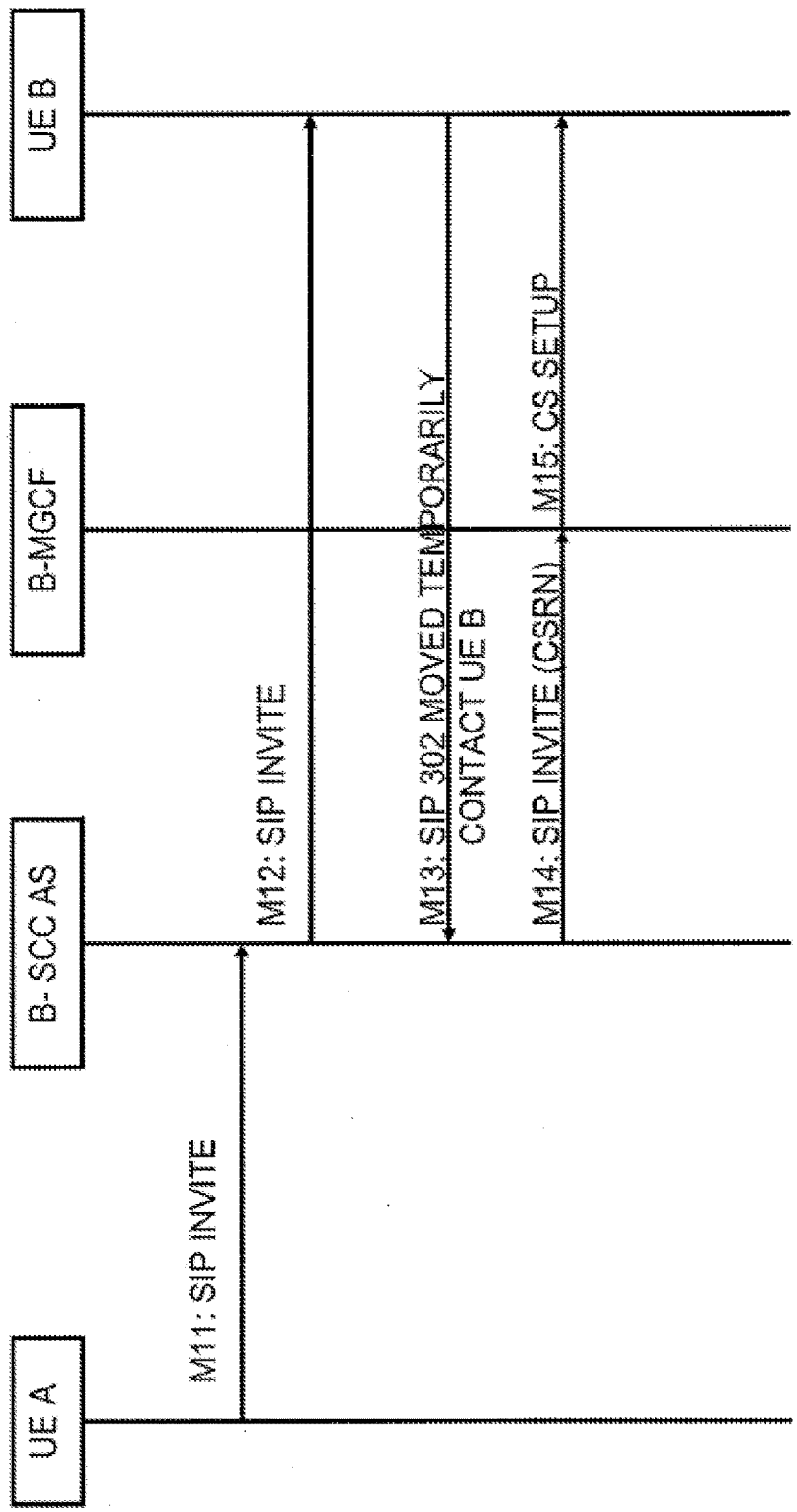
FIG. 1 shows a signaling diagram of a terminating session setup procedure according to an example of an embodiment of the invention.

In the following, examples and embodiments of the present invention are described with reference to the drawings. For illustrating the present invention, the examples and embodiments will be described in connection with a 3GPP system where a communication connection or session to a communication connection terminating node like a UE from an IMS network is to be established or modified. However, it is to be noted that the present invention is not limited to an application in such a system or environment but is also applicable in other network systems, connection types and the like, for example in networks according to 3GPP2 specifications or the like.

A basic system architecture of a communication network where the present invention is applicable may comprise a commonly known architecture of an IMS network supporting ICS. Such a network architecture comprises several control nodes or CSCF which are SIP servers or proxies fulfilling several roles (such as Interrogating CSCF (I-CSCF), Proxy CSCF (P-CSCF), Serving CSCF (S-SCSF)) and used to process SIP signaling packets in the IMS. Furthermore, MGCF, SCC AS and the like are part of the architecture. The general functions and interconnections of these elements are known to those skilled in the art and described in corresponding specifications so that a detailed description thereof is omitted herein. However, it is to be noted that there may be provided several additional network elements and signaling links used for a communication connection than those described below.

A basic system architecture of a communication network may comprise a commonly known architecture of a wired or wireless access network subsystem. Such an architecture comprises one or more access network control units, radio access network elements, access service network gateways or base transceiver stations, with which a mobile station or terminal device as a subscriber's user equipment is capable of communicating via one or more channels for transmitting several types of data. The general functions and interconnections of these elements are known to those skilled in the art and described in corresponding specifications so that a detailed description thereof is omitted herein. However, it is to be noted that there are provided several additional network elements and signaling links used for a communication connection or a call between end terminals and/or servers.

Furthermore, the network elements and their functions described herein may be implemented by software, e.g. by a computer program product for a computer, or by hardware. In any case, for executing their respective functions, correspondingly used devices, such as UE or SCC AS, comprise several means and components (not shown) which are required for control, processing and communication/signaling functionality. Such means may comprise, for example, a processor unit for executing instructions, programs and for processing data, memory means for storing instructions, programs and data, for serving as a work area of the processor and the like (e.g. ROM, RAM, EEPROM, and the like), input means for inputting data and instructions by software (e.g. floppy diskette, CD-ROM, EEPROM, and the like), user interface means for providing monitor and manipulation possibilities to a user (e.g. a screen, a keyboard and the like), interface means for establishing links and/or connections under the control of the processor unit (e.g. wired and wireless interface means, an antenna, etc.) and the like.

FIG. 1 shows a signaling diagram illustrating a terminating session setup procedure according to an example of an embodiment of the invention. In this procedure, the following network elements are indicated to be involved, wherein it is to be noted that additional network parts are used for the call establishment as such. However, for illustrating the present invention and for the sake of simplicity, only those network elements are shown and described whose functionalities are relevant for performing the proposed terminating session setup procedure. The network elements shown are:

- a calling communication connection originating node, such as a UE A,
- a called communication connection terminating node, such as a UE B,
- a MGCF in the network of the called UE B (B-MGCF),
- an application server for service centralization and continuity, such as an SCC AS.

The general functions and structures of these elements are known to those skilled in the art so that a description thereof is omitted here.

In the terminating session setup procedure according to the present example of an embodiment of the invention, when a calling side (the UE A in FIG. 1) wishes to establish, for example, a communication connection with a specific type of media flow, such as audio for speech transmission, it sends a corresponding communication connection initialization message (M11) towards the desired called side, i.e. the communication connection terminating node (the UE B in FIG. 1). When using the IMS, the communication connection initialization message is a SIP INVITE message, for example. The terminating side Service Centralization and Continuity Application Server (B-SCC AS) receives the connection initialization message (SIP INVITE message) from the UE B via other network elements, for example a S-CSCF (not shown).

The B-SCC AS may decide to deliver the call via PS access (PS domain, first domain) towards the called UE B (message M12). In such a case, when receiving the INVITE message, the terminating UE B determines, on the basis of the information included in the INVITE message, such as the connection parameters, media flow indications, access domain to be used etc., whether the PS access, which is selected by the SCC AS, is suitable for voice transmission (audio media flow) or the like. Alternatively or additionally, the UE B checks whether or not the UE B is capable for the defined media flow type, such as VoIP.

In case the determinations in the UE B regarding the capability for the indicated parameters of communication connection leads to a positive result, i.e. that the communication connection can be established with the UE B over the PS access, the call establishment may be completed in a regular manner as defined in several standards, for example.

However, in case that the determination is negative, i.e. that the PS access is not suitable for audio or that the UE is not able to execute the requested connection, the UE B sends a specific negative response (M13) to the requesting B-SCC AS for rejecting the current communication connection initialization request.

According to the present example of the embodiment of the invention, for example, the specific negative response comprises a specific SIP response code indicating that the contact address of the UE B (the called communication connection terminating node) is moved temporarily, i.e. a SIP 302 message. In this SIP 302 message, in addition, in the contact header the address is indicated which is received in the P-Called-Party-ID header of the INVITE request. This means that the UE B instructs the network to re-route the call to the very same destination. Thus, on the basis of the presence of such a "loop", the SCC AS may re-route the call to a CS domain (second domain) of the same subscriber, as described below.

When receiving the (negative) response message from the UE B, the B-SCC AS processes the contents of the message M13 and checks a predetermined set of conditions. In other words, the B-SCC AS determines whether the following conditions are true:

- the connection initialization request message includes a parameter indicating the later rejected media flow type of the communication connection, i.e. for example the original SIP INVITE message includes an SDP parameter indicating audio like m=audio;
- the response message indicates a failure to deliver to the communication connection terminating node, for example, the SIP message 302 (or another SIP message described later) indicates a failure to deliver to the UE B;
- the response message does not indicate that a user of the communication connection terminating node performed an operation to not accept the communication connection (e.g. in case the end user of the UE is not willing to accept the call and performed a corresponding operation at the UE for declining/dropping the call attempt) or that the communication connection terminating node is busy, i.e. that the SIP response message does not indicate a code like SIP 603 (Declined) or SIP 486 (Busy);
- the response message does not indicate another service specific action, such as for example an indication of a different destination address to be used for the re-routing of the call, or another codec for the audio media flow component (e.g. a different destination in a SIP re-routing response, such as SIP 302 and SIP 301 (permanently moved), or an alternative voice codec in SDP in a SIP 488 message);
- a local configuration for the called communication connection terminating node is present, which allows a re-routing to the other communication domain, i.e. that the B-SCC AS has a local configuration for the called user UE B that in the case of rejection the call should be re-routed to CS domain;
- it is assumed that a communication network portion leading to the communication connection terminating node (UE B) is able to deliver the media flow type in question (here: audio) to the communication connection terminating node UE B in the second communication domain (CS domain), i.e. that the B-SCC AS does not have any knowledge about circumstances that e.g. the B-MGCF is not able to deliver the CS call, e.g. that there are any requirements in the request that the B-MGCF could not fulfill.

According to the present example of the embodiment of the invention, for achieving a positive result of the check, it is assumed that the above conditions are all to be met, i.e. there is an AND link between these conditions. Alternatively, there may be also cases where a further example of the embodiment of the invention works wherein one or more of the above conditions can be omitted or where an OR link between at least some of the above conditions can be established. In addition, it is to be noted that the above indicated list is not final, i.e. that also other conditions could be considered in addition or as a supplement for the described conditions, such as charging related conditions or the like.

Depending on the result of the check of the condition set, the B-SCC AS may conduct different further processing. That is, in case the check is positive, i.e. all conditions are met, the SCC AS re-routes the communication connection to the second (CS) domain and sets up a corresponding INVITE request to the CSRN (Circuit Switched Roaming Number) of the UE B. For this purpose, the SCC AS directs a SIP INVITE message with the CSRN to the B-MGCW (message M14) which performs a CS setup procedure with the UE B (message M15).

Otherwise, in case the check is negative, the B-SCC AS returns an indication of the negative (rejecting) response from the UE B backwards towards the calling side (the UE a) (not shown in FIG. 1). By means of this, for example, another application server or the like of the calling UE A may execute corresponding services (e.g. CFNRc (Call Forwarding on Mobile Subscriber Not Reachable), CFB in TAS (Call Forwarding Busy in Telephony Application Server))

Figure 2:
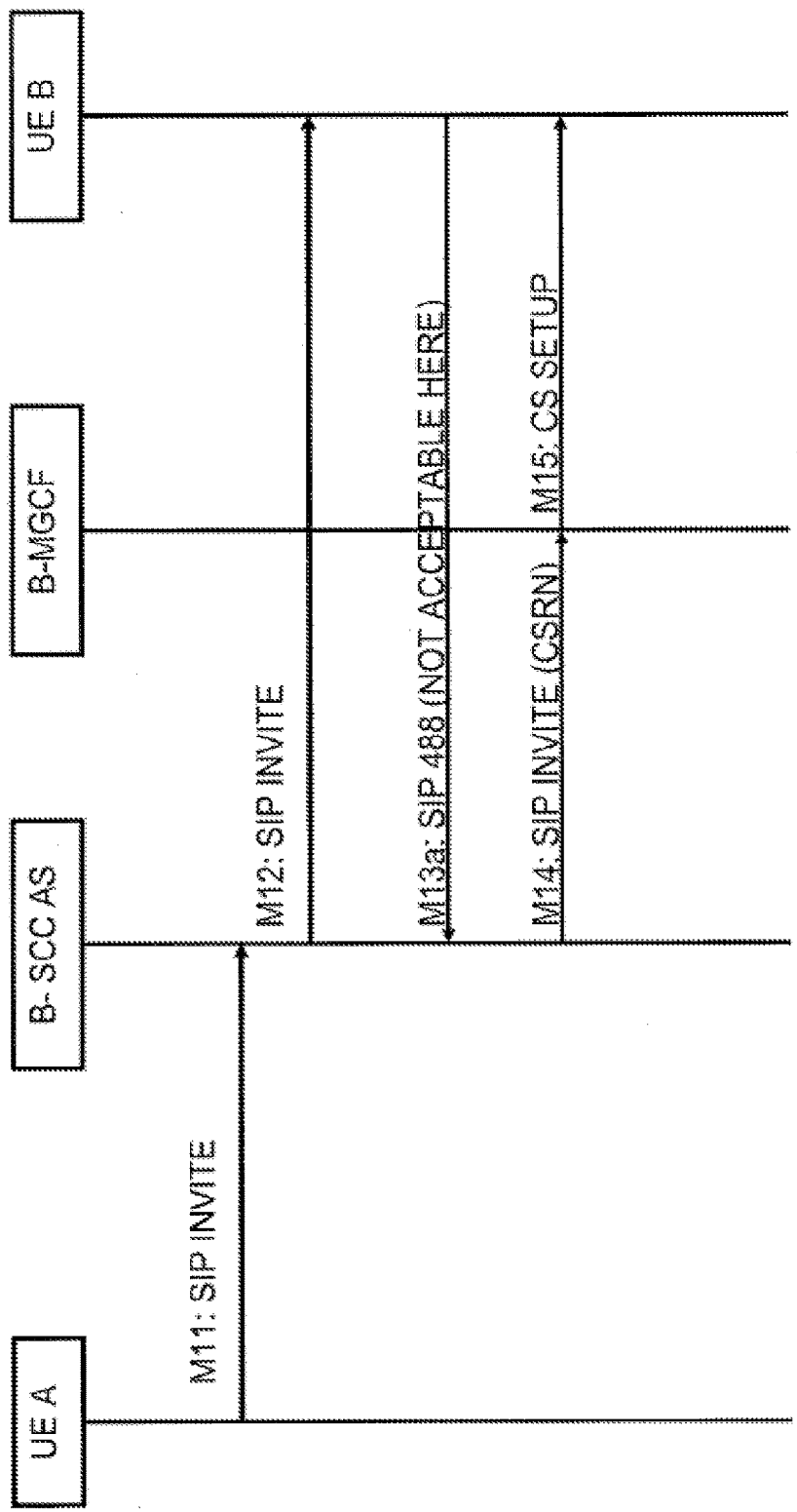
FIG. 2 shows a signaling diagram of a terminating session setup procedure according to an alternativve example of an embodiment of the invention.

Another example of an embodiment of the present application is described in connection with FIG. 2. FIG. 2 shows a further signaling diagram illustrating another example of a terminating session setup procedure according. In this procedure, the network elements and functions are equivalent to those of the example according to FIG. 1, except that of the UE B in connection with message M13a. The description of the equivalent elements and parts is omitted here for the sake of simplicity.

According to the example shown in FIG. 2, after receiving the communication connection initialization message by message M12 and when the UE B decides that the PS access is not suitable for audio or that the UE is not able to execute the requested connection, the UE B sends another specific negative response (M13a) to the requesting B-SCC AS for rejecting the current communication connection initialization request. In this example, the specific negative response comprises a specific SIP response code indicating that the communication connection attempt to the UE B (the called communication connection terminating node) is not acceptable here, e.g. SIP 488 (Not Acceptable Here) response. This message M13a does not include an SDP body with an indication for the media flow type in question, i.e. an m-line indicating audio. This means that the B-SCC AS recognizes that the required PS resources for audio cannot be delivered and therefore the the B-SCC AS should re-route to the CS domain.

In the following, the structure and function of a network element corresponding to the application server for service centralization and continuity (the B-SCC AS) is described in connection with FIGS. 3 and 4.

Figure 3:
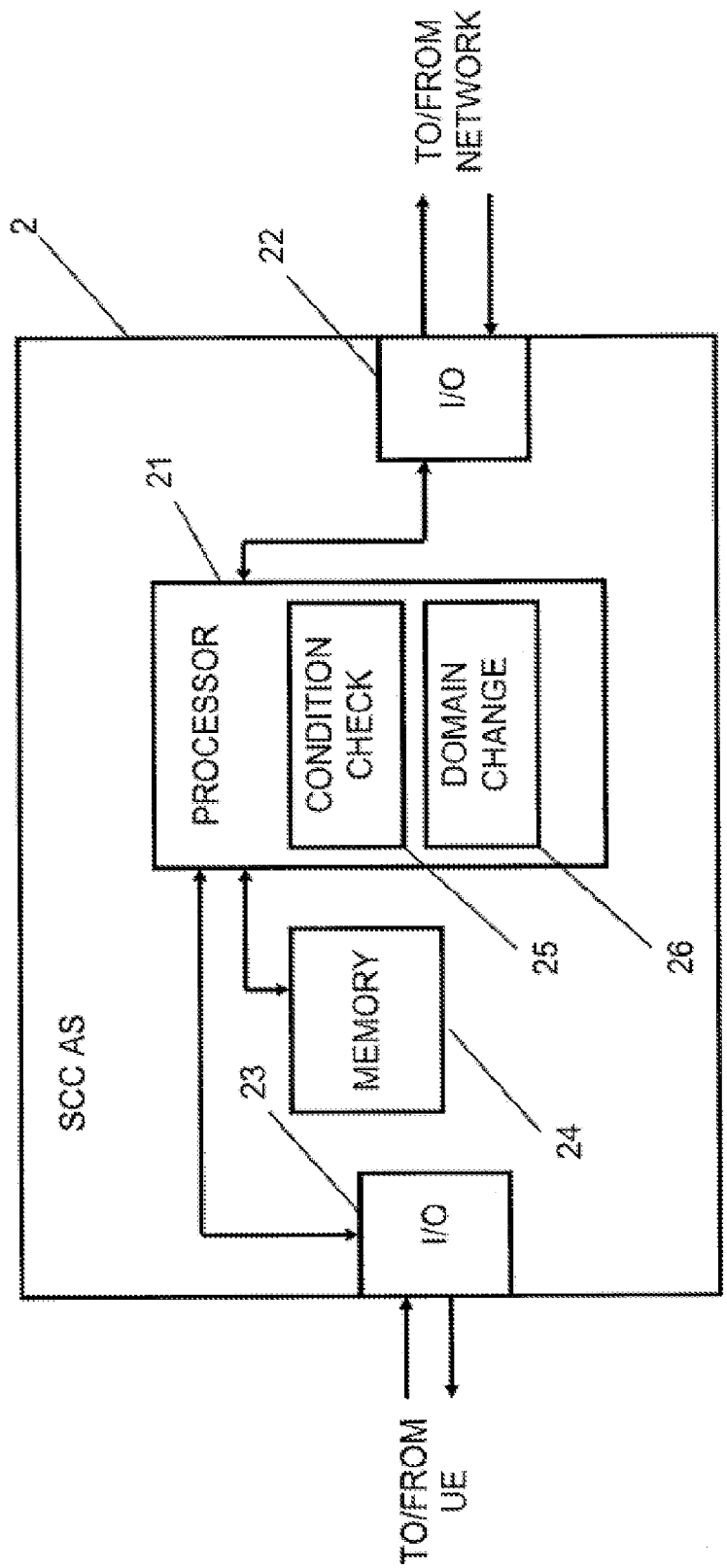
FIG. 3 shows a block circuit diagram of an application server for service centralization and continuity according to an example of an embodiment of the invention.

In FIG. 3, a block circuit diagram of an application server for service centralization and continuity 2, for example the B-SCC AS of FIG. 1, according to an example of an embodiment of the invention is shown. It is to be noted that the application server for service centralization and continuity may comprise several further elements or functions besides those described in connection with FIG. 3 which are omitted herein for the sake of simplicity as they are not essential for understanding the invention.

The application server for service centralization and continuity 2 (referred to as SCC AS hereinafter) according to FIG. 3 comprises a processing function or processor 21, such as a CPU or the like, which executes instructions given by programs or the like related to the processing shown in FIG. 4 (described later). The processor 21 is in particular used for processing information given by the messages M11 and M13/M13a and for generating messages M12 and M14 according to FIGS. 1 and 2. Reference signs 22 and 23 denote input/output (I/O) units connected to the processor 21. The I/O unit 22 may be used for communicating with the network (for example, network elements leading to the calling side of the UE A, wherein the INVITE message M11 may be received from there). The I/O unit 23 may be used for communicating with the UE B (or a intermediate proxy leading to the UE B), for example via the B-MGCF (for example, the INVITE message M12 and M14 may be transmitted via this unit and the response message M13/M13a may be received here). The I/O units 22 and 23 may also be combined in one member, such as a transceiver unit or the like. Reference sign 24 denotes a memory usable, for example, for storing data and programs to be executed by the processor 21 and/or as a working storage of the processor 21. Reference sign 25 denotes a condition check portion for determining whether or not the predetermined condition set is met in case a negative response is received from the UE B, for example. Reference sign 26 denotes a domain change portion which, in reaction of the result of the determination of the condition check portion 25 and the information retrieved from the original INVITE message M11, is adapted to determine to which communication domain the re-routing is to be executed (in the described example, change to the CS domain).

Figure 4:
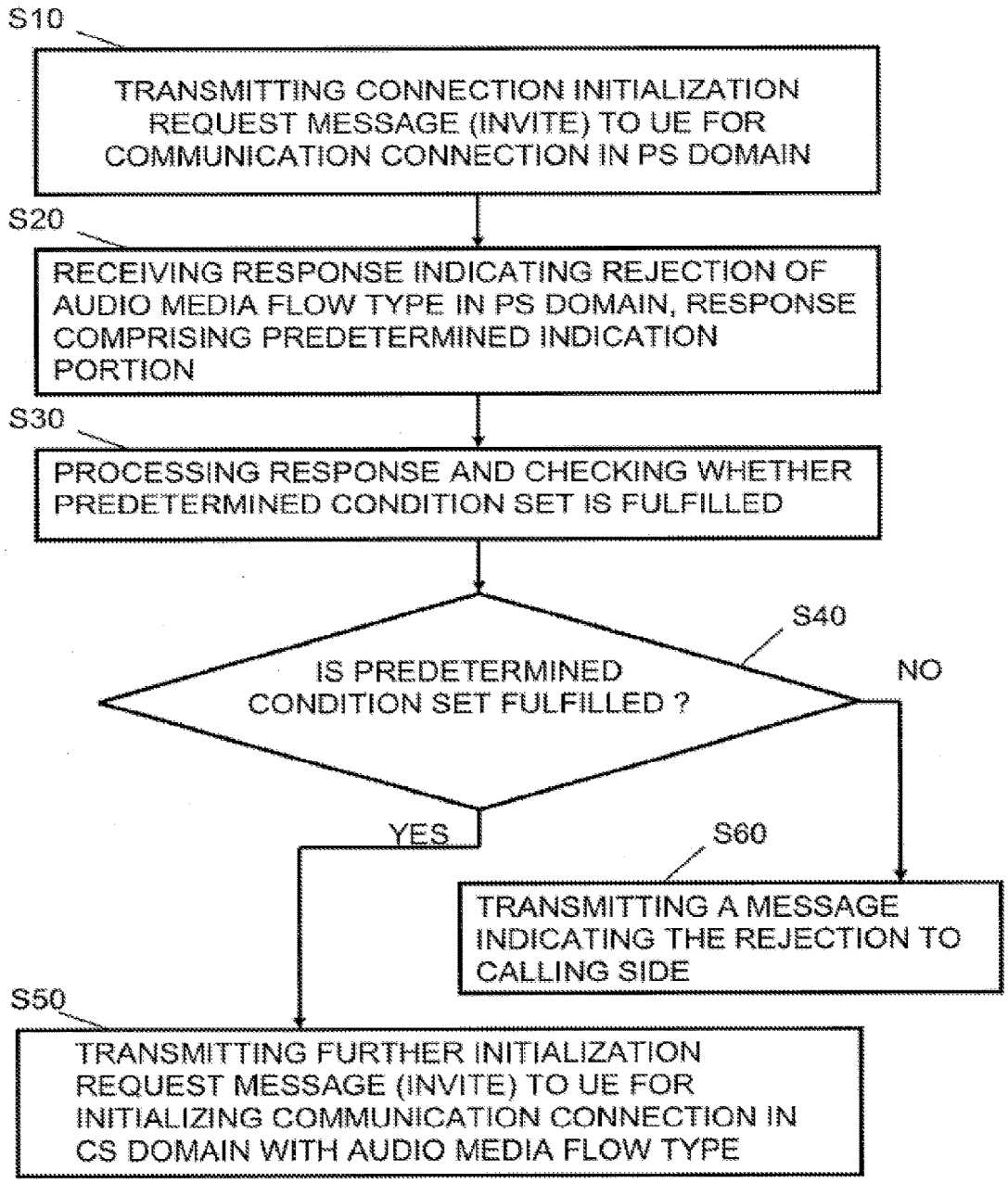
FIG. 4 shows a flow chart of a method executed in a terminating session setup procedure according to an example of an embodiment of the invention.

FIG. 4 shows a flow chart of a method executed by an apparatus comprising the elements and functions of the application server for service centralization and continuity of FIG. 3 in a terminating session setup procedure according to an example of an embodiment of the invention.

In step S10, after receiving a corresponding connection initialization request message from a calling party, e.g. via I/O unit 22, the connection initialization request message (SIP INVITE) is transmitted to the communication connection terminating node (UE B), e.g. via I/O unit 23.

In step S20, a response to the connection initialization request message is received, e.g. via I/O unit 23. It is determined, e.g. by the processor 21, that the response indicates a rejection of the communication connection, i.e. of a media flow type (like audio), in the first communication domain (PS domain). In addition, it is determined that the response comprises a predetermined indication portion, such as a SIP 302 or SIP 488 message portion as described above. Then, when further processing the received response (step S30), it is checked by the processor (i.e. the condition check portion 25), whether the predetermined condition set as described above is met.

If the predetermined condition set is met (step S40, YES), the processor 21 initiates in step S50 a transmission of another connection initialization request message to the communication connection terminating node (UE B) via the I/O unit 23 for initializing a communication connection in a second communication domain (CS domain, selected by domain change portion 26) with the rejected media flow type (audio).

On the other hand, in case the determination in steps S30, S40 is negative (step S40, NO), i.e. if the predetermined condition set is not met, the processor initiates a transmission of a message indicating the rejection of the communication connection to the calling side, i.e. to the communication connection originating node UE A.

In the following, the structure and function of a network element corresponding to the communication connection terminating node (the UE B) is described in connection with FIGS. 5 and 6.

Figure 5:
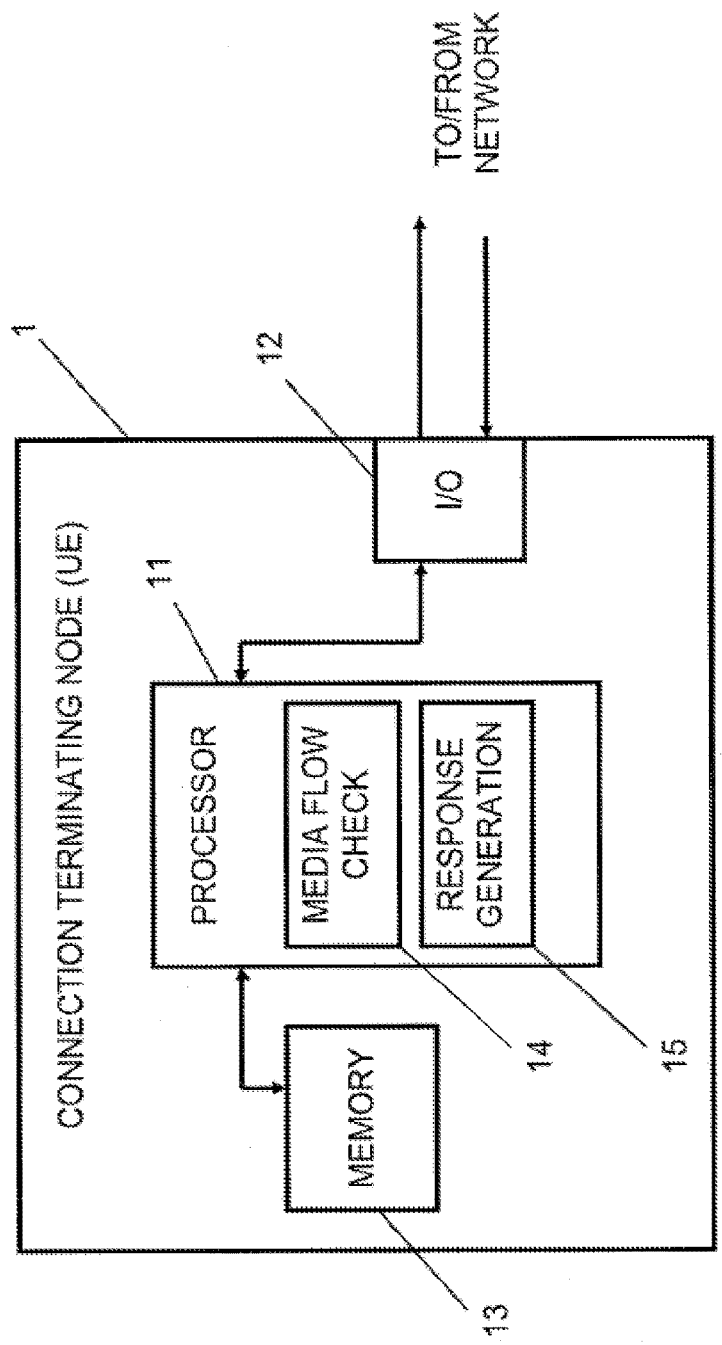
FIG. 5 shows a block circuit diagram of a communication connection terminating node according to an example of an embodiment of the invention.

In FIG. 5, a block circuit diagram of a communication connection terminating node 1, for example the UE B of FIG. 1, according to an example of an embodiment of the invention is shown. It is to be noted that the communication connection terminating node may comprise several further elements or functions besides those described in connection with FIG. 5 which are omitted herein for the sake of simplicity as they are not essential for understanding the invention.

The communication connection terminating node 1 (referred to as UE B hereinafter) according to FIG. 5 comprises a processing function or processor 11, such as a CPU or the like, which executes instructions given by programs or the like related to the processing shown in FIG. 6 (described later). The processor 11 is in particular used for processing information given by the messages M12 and M15 and for generating messages M13/M13a according to FIGS. 1 and 2. Reference sign 12 denotes an input/output (I/O) unit connected to the processor 11. The I/O unit 12 may be used for communicating with the network (for example, the application server for service centralization and continuity (SCC AS) or the MGCW). Reference sign 13 denotes a memory usable, for example, for storing data and programs to be executed by the processor 11 and/or as a working storage of the processor 11. Reference sign 14 denotes a media flow check portion for determining whether or not the communication connection as requested, in particular the media flow types instructed therein, can be executed via a specific communication domain, e.g. the PS domain. Reference sign 15 denotes a response generation portion which, in reaction of the result of the determination of the media flow check portion 14 and the information retrieved from the original INVITE message M12, is adapted to generate the response to the connection initialization request message wherein the response indicates a rejection of the communication connection, i.e. of a media flow type (like audio), in the first communication domain (PS domain) and comprises the predetermined indication portion, such as a SIP 302 or SIP 488 message portion.

Figure 6:
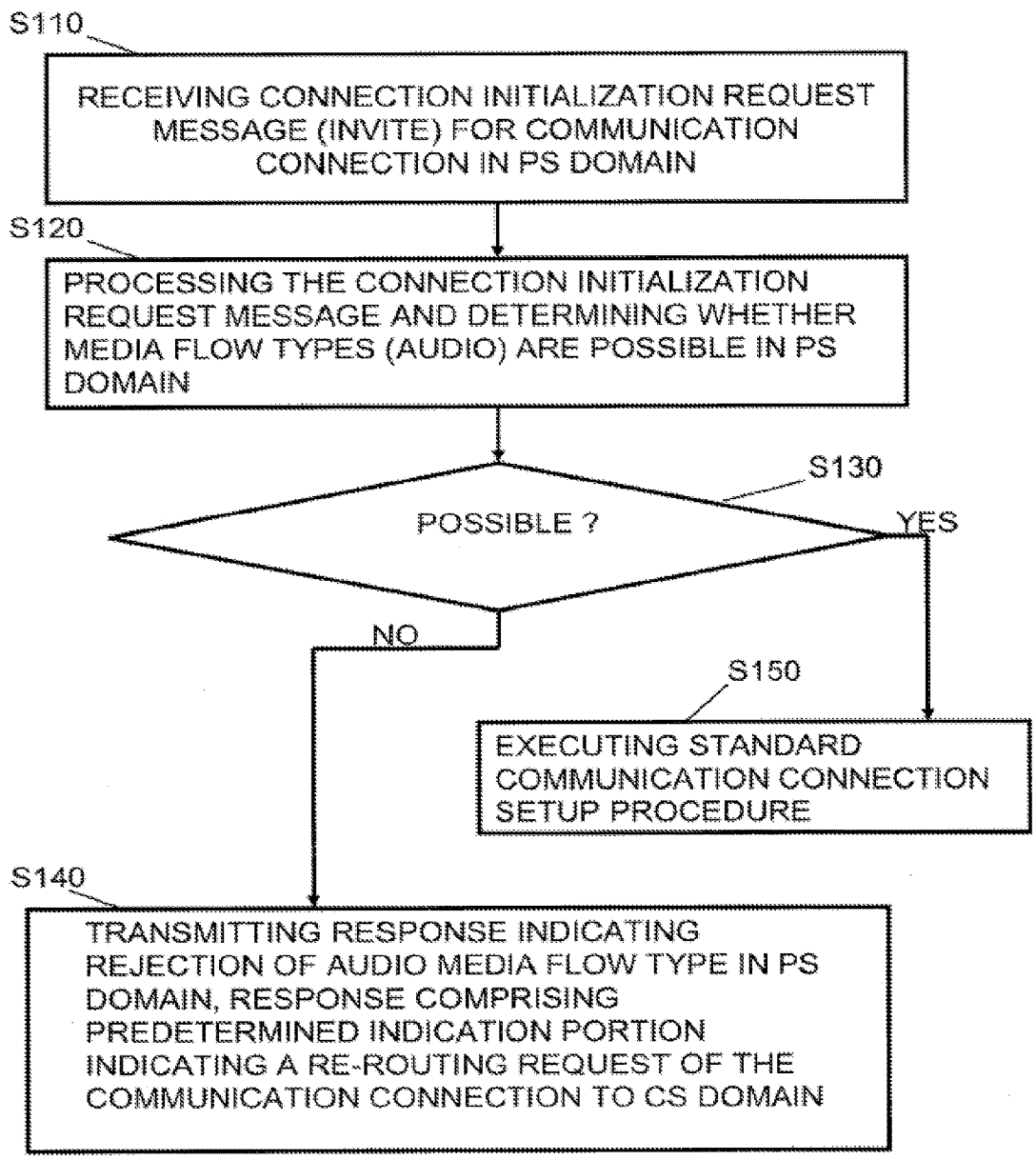
FIG. 6 shows a flow chart of a method executed in a terminating session setup procedure according to an example of an embodiment of the invention.

FIG. 6 shows a flow chart of a method executed by an apparatus comprising the elements and functions of the UE B of FIG. 5 in a terminating session setup procedure according to an example of an embodiment of the invention.

In step S110, a connection initialization request message from a calling party (i.e. the SCC AS) is received, e.g. via I/O unit 12.

In step S120, the connection initialization request message is processed by the processor 11 wherein it is determined whether or not a communication connection as requested is possible. As described above, for example, it is determined by the media flow check portion 14 whether or not the UE B is capable of performing the requested connection type and/or whether or not the PS access is suitable for the connection or the media flow type requested (e.g. audio). a response to the connection initialization request message is received, e.g. via I/O unit 23. It is determined, e.g. by the processor 21, that the response indicates a rejection of the communication connection, i.e. of a media flow type (like audio), in the first communication domain (PS domain).

If it is determined that the communication connection as requested is possible (step S130: YES), then standard communication connection setup procedures may be executed in a step S150.

Otherwise, in case it is determined that the communication connection as requested is not possible (step S130: NO), then a negative response is generated by the response generation portion 15 for rejecting the communication connection (e.g. the audio media flow type) in the first (PS) domain. The response generated by the response generation portion 15 comprises a predetermined indication portion, such as a SIP 302 or SIP 488 message portion as described above, for instructing a re-routing of the call to the second (CS) domain.

It is to be noted that in the above described examples the determination that the communication connection as requested is not possible and the transmission of the corresponding negative response, for example in the form of a SIP 302 or SIP 488 message is executed by the UE B itself. However, the present invention is not limited to such a configuration. For example, the determination of whether or not the PS access is suitable for the requested communication connection can be also effected before the terminating node (the UE B) in the network, e.g. in an intermediate proxy like a P-CSCF which, for example, can not accept the request. This intermediate proxy then returns the negative response. The further processing of the SCC AS, for example, is equivalent to that described in connection with FIG. 1 or FIGS. 3 and 4, while the function and construction of the intermediate proxy corresponds to those depicted in FIGS. 5 and 6 (related to the UE B).

For the purpose of the present invention as described herein above, it should be noted that an access technology may be any technology by means of which a user equipment can access an access network (e.g. via a base station or generally an access node). Any present or future technology, such as WLAN (Wireless Local Access Network), WiMAX (Worldwide Interoperability for Microwave Access), BlueTooth, Infrared, and the like may be used; although the above technologies are mostly wireless access technologies, e.g. in different radio spectra, access technology in the sense of the present invention may also imply wirebound technologies, e.g. IP based access technologies like cable networks or fixed lines but also circuit switched access technologies; access technologies may be distinguishable in at least two categories or access domains such as packet switched and circuit switched, but the existence of more than two access domains does not impede the invention being applied thereto, an access network may be any device, apparatus, unit or means by which a station, entity or other user equipment may connect to and/or utilize services offered by the access network; such services include, among others, data and/or (audio-) visual communication, data download etc.;

a user equipment (or mobile station) may be any device, apparatus, unit or means by which a system user may experience services from an access network such as a mobile phone, personal digital assistant PDA, or computer;

method steps likely to be implemented as software code portions and being run using a processor at a network element or terminal (as examples of devices, apparatuses and/or modules thereof, or as examples of entities including apparatuses and/or modules therefor), are software code independent and can be specified using any known or future developed programming language as long as the functionality defined by the method steps is preserved;

generally, any method step is suitable to be implemented as software or by hardware without changing the idea of the invention in terms of the functionality implemented;

method steps and/or devices, apparatuses, units or means likely to be implemented as hardware components at a terminal or network element, or any module(s) thereof, are hardware independent and can be implemented using any known or future developed hardware technology or any hybrids of these, such as MOS (Metal Oxide Semiconductor), CMOS (Complementary MOS), BiMOS (Bipolar MOS), BiCMOS (Bipolar CMOS), ECL (Emitter Coupled Logic), TTL (Transistor-Transistor Logic), etc., using for example ASIC (Application Specific IC (Integrated Circuit)) components, FPGA (Field-programmable Gate Arrays) components, CPLD (Complex Programmable Logic Device) components or DSP (Digital Signal Processor) components; in addition, any method steps and/or devices, units or means likely to be implemented as software components may for example be based on any security architecture capable e.g. of authentication, authorization, keying and/or traffic protection;

devices, apparatuses, units or means can be implemented as individual devices, apparatuses, units or means, but this does not exclude that they are implemented in a distributed fashion throughout the system, as long as the functionality of the device, apparatus, unit or means is preserved, an apparatus may be represented by a semiconductor chip, a chipset, or a (hardware) module comprising such chip or chipset; this, however, does not exclude the possibility that a functionality of an apparatus or module, instead of being hardware implemented, be implemented as software in a (software) module such as a computer program or a computer program product comprising executable software code portions for execution/being run on a processor;

a device may be regarded as an apparatus or as an assembly of more than one apparatus, whether functionally in cooperation with each other or functionally independently of each other but in a same device housing, for example.

As described above, there is proposed a method and corresponding apparatuses allowing a change from a packet switched communication domain to a circuit switched communication domain. When a user equipment as a connection terminating point determines receives a connection initialization message with a media flow, such as audio, which can no be delivered by the packet switched access, it sends a specific response rejecting the connection via the packet switched access to an application server for service centralization and continuity. In the application server, it is checked whether several conditions are met in order to determine whether the communication connection comprising the media flow is allowed to be changed to the circuit switched domain. If yes, the communication connection is changed from the packet switched communication domain to the circuit switched communication domain.

Although the present invention has been described herein before with reference to particular embodiments thereof, the present invention is not limited thereto and various modifications can be made thereto.

The invention claimed is:

1. An apparatus comprising:
    a transmitter configured to transmit a connection initialization request message to a communication connection terminating node for initializing a communication connection in a first communication domain;
    a receiver configured to receive a response to the connection initialization request message, the response indicating a rejection of a media flow type of the communication connection in the first communication domain, the response comprising a predetermined indication portion, the predetermined indication portion indicating a re-routing request of the communication connection to a second communication domain; and
    a processor configured to process the received response.

2. The apparatus according to claim 1, wherein said processor is further configured, if a predetermined condition set is not met, to at least cause a transmission of a message indicating the rejection to a communication connection originating node.

3. The apparatus according to claim 1, wherein the predetermined indication portion comprises an information that a contact address of the communication connection terminating node is temporarily changed.

4. The apparatus according to claim 3, wherein the predetermined indication portion further comprises address information included in the connection initialization request message.

5. The apparatus according to claim 4, wherein the processor is further configured to at least determine, based on the address information, that the communication connection is to be re-routed to the same communication connection terminating node in the second communication domain.

6. The apparatus according to claim 1, wherein the predetermined indication portion comprises an information that a communication connection attempt is not acceptable here.

7. The apparatus according to claim 2, wherein the predetermined condition set comprises at least one of a condition that the connection initialization request message includes a parameter indicating a later rejected media flow type of the communication connection, a condition that the response indicates a failure to deliver to the communication connection terminating node, a condition that the response does not indicate that a user of the communication connection terminating node performed an operation to not accept the communication connection or that the communication connection terminating node is busy, a condition that the response does not indicate another service specific action, a condition that a local configuration for a called communication connection terminating node is present in the apparatus, which allows a re-routing to the second communication domain, and a condition that an ability of a communication network portion leading to the communication connection terminating node to deliver the media flow type to the communication connection terminating node in the second communication domain is assumed.

8. The apparatus according to claim 1, wherein the first communication domain is based on a packet switched transmission and the second communication domain is based on a circuit switched transmission.

9. The apparatus according to claim 1, wherein the specific media flow type is an audio media flow type.

10. The apparatus according to claim 1, wherein the apparatus is comprised by an application server for service centralization and continuity.

11. A method comprising:
   transmitting a connection initialization request message to a communication connection terminating node for initializing a communication connection in a first communication domain;
   receiving a response to the connection initialization request message, the response indicating a rejection of a media flow type of the communication connection in the first communication domain, the response comprising a predetermined indication portion, the predetermined indication portion indicating a re-routing request of the communication connection to a second communication domain; and
   processing the received response.

12. The method according to claim 11, further comprising:
   if a predetermined condition set is not met, transmitting a message indicating the rejection to a communication connection originating node.

13. The method according to claim 11, wherein the predetermined indication portion comprises an information that a contact address of the communication connection terminating node is temporarily changed.

14. The method according to claim 13, wherein the predetermined indication portion further comprises address information included in the connection initialization request message.

15. The method according to claim 14, further comprising:
   determining, based on the address information, that the communication connection is to be re-routed to the same communication connection terminating node in the second communication domain.

16. The method according to claim 11, wherein the predetermined indication portion comprises an information that a communication connection attempt is not acceptable here.

17. The method according to claim 12, wherein the predetermined condition set comprises at least one of a condition that the connection initialization request includes a parameter indicating a later rejected media flow type of the communication connection, a condition that the response indicates a failure to deliver to the communication connection terminating node, a condition that the response does not indicate that a user of the communication connection terminating node performed an operation to not accept the communication connection or that the communication connection terminating node is busy, a condition that the response does not indicate another service specific action, a condition that a local configuration for a called communication connection terminating node is present in the apparatus, which allows a re-routing to the second communication domain, and a condition that an ability of a communication network portion leading to the communication connection terminating node to deliver the media flow type to the communication connection terminating node in the second communication domain is assumed.

18. The method according to claim 11, wherein the first communication domain is based on a packet switched transmission and the second communication domain is based on a circuit switched transmission.

19. The method according to claim 11, wherein the specific media flow type is an audio media flow type.

20. The method according to claim 11, wherein the method is implemented in an application server for service centralization and continuity.

* * * * *